(12) United States Patent
Feuerstein et al.

(10) Patent No.: US 8,071,646 B2
(45) Date of Patent: *Dec. 6, 2011

(54) OMEGA 3 FATTY ACID FORMULATIONS

(75) Inventors: Seth D. Feuerstein, New Haven, CT (US); Ann Coric, Madison, CT (US); Louis C. Sanfilippo, Orange, CT (US)

(73) Assignee: Cenestra LLC, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/607,587

(22) Filed: Oct. 28, 2009

(65) Prior Publication Data

US 2010/0112047 A1 May 6, 2010

Related U.S. Application Data

(63) Continuation of application No. 11/613,612, filed on Dec. 20, 2006, now Pat. No. 7,652,068.

(60) Provisional application No. 60/752,148, filed on Dec. 20, 2005.

(51) Int. Cl.
*A61K 31/185* (2006.01)
*A61K 31/21* (2006.01)
*A61K 35/60* (2006.01)
*A61K 31/20* (2006.01)

(52) U.S. Cl. .................. 514/560; 514/506; 514/578

(58) Field of Classification Search .................. None
See application file for complete search history.

(56) References Cited

U.S. PATENT DOCUMENTS

| | | | |
|---|---|---|---|
| 5,502,077 A | 3/1996 | Breivik et al. | |
| 5,656,667 A | 8/1997 | Breivik et al. | |
| 5,698,594 A | 12/1997 | Breivik et al. | |
| 6,365,176 B1 * | 4/2002 | Bell et al. | |
| 6,624,195 B2 | 9/2003 | Horrobin | |
| 2003/0012827 A1 | 1/2003 | Stoll | |
| 2005/0245610 A1 * | 11/2005 | Verboom et al. | |
| 2006/0211762 A1 * | 9/2006 | Rongen et al. | |

FOREIGN PATENT DOCUMENTS

| | | |
|---|---|---|
| EP | 1157692 | 11/2001 |
| WO | 0023069 | 4/2000 |
| WO | 2005070411 A1 | 8/2005 |
| WO | 2006017692 | 2/2006 |
| WO | 2006085144 A2 | 8/2006 |

OTHER PUBLICATIONS

Dorland's Medical Dictionary for Healthcare Consumers, "dyslipidemia", 2007, pp. 1 of 1.*

Perry, "Omega-3 for bipolar disorder—Restoring the balance", Sep. 2001, Food and Behaviour Research, pp. 1-9 of 9, downloaded from "http://www.fabresearch.org/uploads/1503/2001%20Andrew%20Stoll%20Interview%20-%20Omega-3%20and%20Bipolar.pdf".*

Stoll, The Omega-3 Connection, Simon & Schuster. 2001, pp. 212-215 provided.*

OmegaBrite® omega-3 supplement (pp. 1-4 of 4, downloaded from "http://omegabrite.com" on Sep. 10, 2008, publicly known on or prior to 2001 as evidenced by disclosure of the product by Stoll, supra.*

Rumsfeld, J.S. and P.M. Ho. "Depression and Cardiovascular Disease: A Call for Recognition," Circulation (2005) 111: 250-253.

Viachopoulos, C. et al. "Acute System Inflammation Increases Artertial Stiffness and Decreases Wave Reflections in Healthy Individuals," Circulation (2005) 112: 2193-2220.

Pharmaceutical Grade Fish Oil, Product Reviews [Online] Oct. 14, 2003, XP002431628 Retrieved from the Internet: URL:http://www.fishoilreview.com/[retrieved on Apr. 26, 2007].

Nakamura K et al: "Influence of preoperative administration of omega-3 fatty acid-enriched supplement on inflammatory and immune responses in patients undergoing major surgery for cancer" Nutrition, Nutrition, Burbank CA, US, vol. 21, No. 6, Jun. 2005, pp. 639-649, XP004940931 ISSN: 0899-9007.

Moyard: "An Introduction to dietary/supplemental omega-3 fatty acids for general health and prevention: Part II" Urologic Oncology, Elsevier, New York, NY US, vol. 23, No. 1, Jan. 2005, pp. 36-48, XP004883101 ISSN: 1708-1439.

Sontrop et al: "omega-3 polyunsaturated fatty acids and depression: A review of the evidence and a methodological critique" Preventive Medicine, Academic Press, XX, vol. 42, No. 1, Dec. 7, 2005, pp. 4-13, XP005291367 ISSN: 0091-7435/.

Defilippis et al: "Understanding omega-3's" American Heart Journal, Mosby-Year Book Inc., St. Louis, MO, US, vol. 151, No. 3, Mar. 2006, pp. 564-570, XP005587549 ISSN: 0002-8703.

International Search Report for International Application No. PCT/US2006/048696. Mailed May 23, 2007.

Written Opinion of the International Search Authority for International Application No. PCT/US2006/048696. Mailed May 23, 2007.

Barnett et al., Annals of Thoracic Surgery, 2003, vol. 76, pp. 726-731.

"Causes of Depression", Depression.com, 1 page, downloaded from "http://www.depression.com/causes_of_depression.html" on Sep. 11, 2008.

* cited by examiner

*Primary Examiner* — James D Anderson
*Assistant Examiner* — Gregg Polansky
(74) *Attorney, Agent, or Firm* — Hogan Lovells US LLP

(57) ABSTRACT

The present invention provides highly purified omega-3 fatty acid formulations. Certain formulations provided herein contain greater than 85% omega-3 fatty acids by weight. Certain other formulations provided herein contain EPA and DHA in a ratio of from about 4.01:1 to about 5:1. The invention also provides methods of using the dosage forms to treat a variety of cardiovascular, autoimmune, inflammatory, and central nervous system disorders by administering a formulation of the invention to a patient in need thereof.

27 Claims, 2 Drawing Sheets

FIGURE 1. scores for a patient before and after treatment with an omega-3 fatty acid formulation containing EPA and DHA in a 4.09:1 ratio.
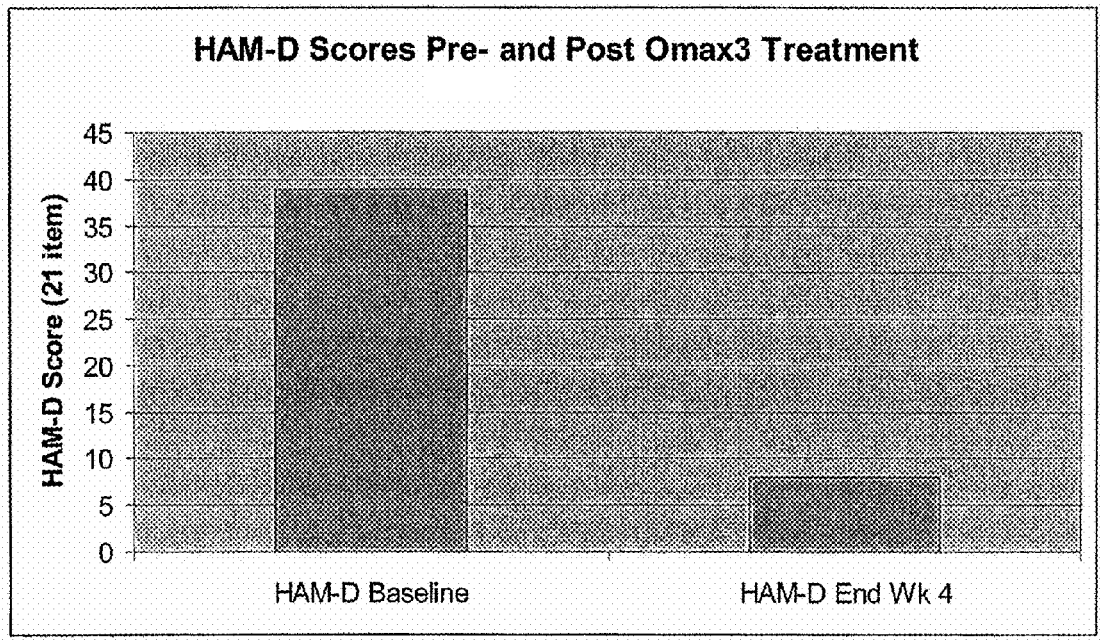

FIGURE 2. Hair Growth Data
2a. Hair Prior to Omax3 Treatment
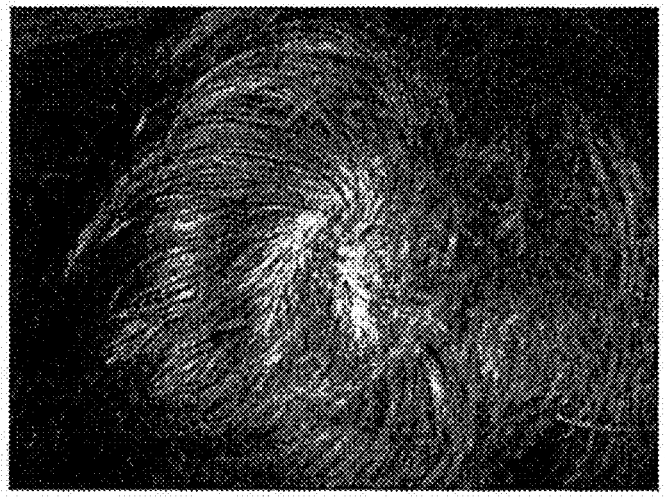
2b. Hair Growth with 41 Days Omax3 Treatment
2c. Hair Growth with 87 Days Omax3 Treatment
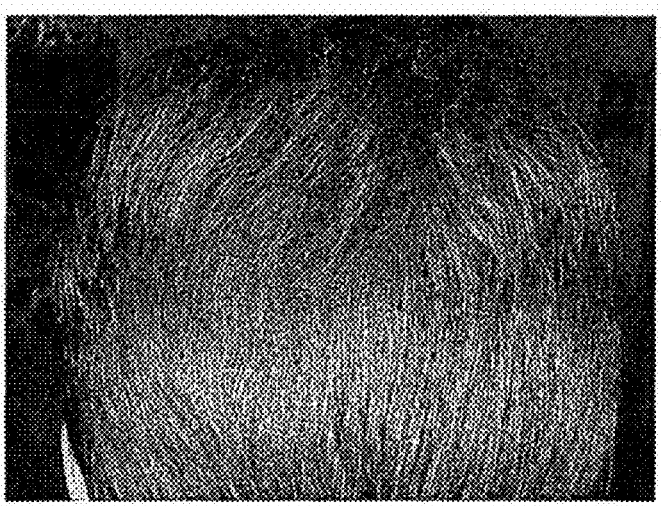

OMEGA 3 FATTY ACID FORMULATIONS

CROSS REFERENCE TO RELATED APPLICATIONS

This application is a continuation of U.S. patent application Ser. No. 11/613,612, filed Dec. 20, 2006, now U.S. Pat. No. 7,652,068, and further claims the benefit of priority from U.S. Provisional Patent Application No. 60/752,148 filed Dec. 20, 2005.

FIELD OF THE INVENTION

The present invention provides highly purified omega-3 fatty acid formulations. Unit dosage forms of the omega-3 fatty acid formulations are provided herein. The invention also provides methods of using the dosage forms to treat a variety of cardiovascular, autoimmune, inflammatory, central nervous system disorders, or chronic pain by providing a formulation of the invention to a patient in need thereof.

BACKGROUND

Omega-3 fatty acids are often referred to as "essential" fatty acids (EFAs) because they are needed for human health but are not sufficiently produced by the body alone. The two major health promoting omega-3 polyunsaturated fatty acids are eicosapentaenoic acid (EPA) and docosaliexaenoic acid (DHA). EPA and DHA are naturally found in certain cold-water fatty fish such as salmon, tuna, and mackerel. They can also be derived in the body from alpha-linolenic acid (ALA), which is an omega-3 fatty acid found in certain seeds and plant-based oils. However, the body is very inefficient at converting ALA into EPA and DHA.

The modern diet is typically deficient in omega-3 essential fatty acids and has become overloaded with pro-inflammatory omega-6 fatty acids, especially arachidonic acid. This heavy imbalance of omega-6 to omega-3 fatty acids in the modern diet is thought to lead to an overall inflammatory state that contributes to certain diseases. The increased consumption of vegetable oils and shortenings, beef, and dairy is one of the major reasons for the high amount of omega-6 fatty acids in the diet and the imbalance between omega-6 to omega-3 fatty acids. The North American population, in particular, has among the lowest dietary intake of omega-3 fatty acids found in the world and the highest amount of the pro-inflammatory omega-6 fatty acids.

Recent scientific developments have shown that the omega-3 fatty acids, in particular EPA and DHA, play a vital role in central nervous system, cognitive, cardiovascular, joint, immune and metabolic function. EPA and DHA not only protect good overall physical and emotional health, but also can reduce the risk of cardiac disease and exert powerful anti-inflammatory effects that can help treat certain diseases. The benefits of EPA and DHA have been studied across a wide range of illnesses, including, but not limited to heart disease, high cholesterol, hypertension, arthritis, back pain, osteoporosis, psoriasis, lupus, Crohn's Disease, back pain, dry eyes, depression, bipolar disorder, ADHD, and stress-related disorders. Omega-3 fatty acids have also been shown to be important in pregnant women and infants, where their depletion may lead to visual or central nervous system problems.

Adequate amounts of omega 3 fatty acids including EPA and DHA can be obtained in the diet from cold-water fatty fish such as salmon, tuna, and mackerel. However larger fish species may contain high levels of mercury, polychlorinated biphenyls (PCBs), dioxins or other contaminants. Thus achieving an optimal amount of omega-3 fatty acids through the intake of fish alone raises a number of safety concerns. Fatty acids supplements are available. However, conventional over-the-counter omega-3 fatty acid supplements contain relatively impure material and are typically only about 30% omega 3 fatty acids. This low purity leads to inadequate dosing of essential fatty acids unless a large number of dosage units are consumed each day. Additionally research suggests that the EPA:DHA ratio is important for efficacy. Currently available omega 3 fatty acid preparations, such as the prescription omega-3 medication OMACOR are formulated for cardiovascular use and contain approximately EPA and DHA in an approximately 3:2 ratio. Other omega-3 formulations are intended primarily for treatment of mental health disorders and very high levels of EPA and little or no DHA. The EPA:DHA ratios for these omega-3 formulations is 7:1 or higher. An intermediate ratio EPA:DHA ratio is considered ideal for treatment of a broad range of cardiovascular, autoimmune, inflammatory, and central nervous system disorders. There remains a need for a highly purified omega-3 dosage form having an EPA:DHA ratio of greater than 3:2 and less than 7:1. The present invention fulfills this need and provides related advantages, which are described herein.

SUMMARY OF THE INVENTION

The invention provides a highly purified omega-3 fatty acid formulation comprising EPA and DHA in a weight to weight ratio from about 3.5:1 to about 6.99 to 1. Formulations having other EPA to DHA weight to weight ratios are also provided and are described in greater detail below. The invention also provides highly purified omega-3 fatty acid formulations in which the content of EPA and DHA, taken together, is greater than 84% of the formulation by weight, and the omega-3 fatty acids comprise greater than 90% of the formulation by weight.

The invention also provides dosage forms of such formulations comprising at least 50 mg DHA and at least 300 mg EPA in a unit dosage form. Dosage forms containing other amount of EPA and DHA are also described herein.

Packed omega-3 formulations comprising one or more omega-3 unit dosage forms of the invention together with instructions for using the formulation to treat or prevent a cardiovascular disorder, feeding disorder, central nervous system disorder, autoimmune disorder, inflammatory disorder or chronic pain are provided by the invention.

Methods of using the highly purified omega-3 fatty acid formulations described herein to treat or prevent a cardiovascular disorder, feeding disorder, central nervous system disorder, autoimmune disorder, inflammatory disorder or chronic pain are provided by the invention.

BRIEF DESCRIPTION OF THE DRAWINGS

FIG. 1. HAM-D scores for a patient before and after treatment with an omega-3 fatty acid formulation containing EPA and DHA in a 4.09:1 ratio.

FIG. 2. Hair growth for patient before and after 41 days and 87 days treatment with omega-3 fatty acid formulation containing EPA and DHA in a 4.09:1 ratio.

DETAILED DESCRIPTION OF THE INVENTION

Terminology

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

An "active agent" means a compound (including EPA or DHA), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound or salt, crystalline forms, non-crystalline forms, and any polymorphs of the compound are included. Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

A "cardiovascular surgical procedure" is any surgery on the heart, veins or arteries. Such procedures includes coronary artery bypass surgery, heart transplant, heart valve surgery, valve replacement, mitral valve repair or replacement, tricupsid valve repair or replacement, septal myectomy, aortic valve repair, repair of congenital heart anomalies, ventricular restoration, and surgical procedures to treat aneurysms and thromboses.

"Cardiotomy" is any surgical procedure in which an incision is made in the heart.

"DHA" is docosahexaenoic acid and "EPA" is eicosapentaenoic acid. The terms EPA and DHA are used to indicate both the triglyceride and esterified forms of these fatty acids unless the triglyceride or esterified form is clearly indicated by the context. DHA and EPA also include pharmaceutically acceptable fatty acid salts.

A "dosage form" means a unit of administration of an active agent. Examples of dosage forms include tablets, capsules, particularly gel and liquid capsules, suspensions, liquids, candy and chewable formulations, emulsions, creams, ointments, suppositories, and the like.

The term "effective amount" or "therapeutically effective amount" means an amount effective, when administered to a patient, to provide any therapeutic benefit. A therapeutic benefit may be an amelioration of symptoms, e.g., an amount effective to decrease the symptoms of a central nervous system disorder, an autoimmune disorder, chronic pain, an inflammatory disorder, or cardiovascular disease. In certain circumstances a patient may not present symptoms of a condition for which the patient is being treated. A therapeutically effective amount of an active agent may also be an amount sufficient to provide a significant positive effect on any indicium of a disease, disorder, or condition, e.g. an amount sufficient to significantly reduce the frequency and severity of symptoms. A significant effect on an indicium of a disease, disorder, or condition is statistically significant in a standard parametric test of statistical significance, for example Student's T-test, where p.ltoreq.0.05. An "effective amount" or "therapeutically effective amount" of the omega-3 formulations provided herein may also be an amount of about of the formulation or of any dosage amount approved by a governmental authority such as the U.S. FDA, for use in treatment. In some embodiments amounts an amount of the formulations provided herein sufficient to provide 900 mg EPA and 150 mg DHA daily, or 990 mg EPA and 190 mg DHA daily, or 1050 mg EPA and 240 mg DHA daily or 1125 mg EPA and 250 mg DHA daily of omega-3 fatty acids in an adult human patient is an "effective amount" or "therapeutically effective amount".

"Efficacy" means the ability of an active agent administered to a patient to produce a therapeutic effect in the patient.

"Gel capsule" means any soft gelatin, liquid-filled capsule that contains a liquid, liquid suspension, solution, gel, or emulsion.

"Liquid capsule" is a capsule with a hard or soft capsule shell filled with a non-solid formulation. The formulation may be for example a liquid, solution, suspension, emulsion or gel.

A "patient" means a human or non-human animal in need of medical treatment. Medical treatment can include treatment of an existing condition, such as a disease or disorder, prophylactic or preventative treatment, or diagnostic treatment. In some embodiments the patient is a human patient. Patients also includes veterinary patients, dogs, cats and horses are particularly included.

"Providing" means giving, administering, selling, distributing, transferring (for profit or not), manufacturing, compounding, or dispensing.

"Salts" as used herein describes "pharmaceutically acceptable salts" of omega-3 fatty acids and other active agents discussed herein and also includes solvates and hydrates of such active agents. The active agent may be modified by making non-toxic acid or base addition salt thereof. Examples of pharmaceutically acceptable salts include mineral or organic acid addition salts of basic residues such as amines; alkali or organic addition salts of acidic residues; and the like, and combinations comprising one or more of the foregoing salts. The pharmaceutically acceptable salts include non-toxic salts and the quaternary ammonium salts of the active agent. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts. Pharmaceutically acceptable organic salts include salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH.sub.2).sub.n—COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, aspharginate, glutamate, and the like; and combinations comprising one or more of the foregoing salts.

A "second myocardial infarction" is any myocardial infarction that is not the initial or first myocardial infarction experienced by the patient.

Pharmaceutical Formulations

The omega-3 fatty acid formulations provided herein may be provided to a patient in any of number of pharmaceutically acceptable oral dosage forms. Preferably the omega-3 fatty acids should be orally administered in the form of pills, tablets, or gel capsules or the like. However, the administration could also be through any other route where the active ingredients may be efficiently absorbed and utilized, e.g. intravenously, subcutaneously, rectally, vaginally or topically. Also included herein are pharmaceutical compositions, comprising pharmaceutical formulations in a unit dosage form. In such dosage forms, the formulation is subdivided into suitably sized unit doses containing appropriate quantities of the omega-3 fatty acids, an effective amount to achieve the desired purpose.

Accordingly the invention provides capsule, tablet, liquid, syrup, suspensions, sublingual, candy, and chewable dosage forms of the omega-3 fatty acid formulations. The invention includes dosage forms in which the EPA and DHA fatty acids are in the triglyceride form, the esterified form, particularly the ethyl ester form, and in which the fatty acids are in the form of acid salts.

The invention also includes methods for making pharmaceutical compositions comprising the omega-3 formulations described herein.

Pharmaceutical dosage forms may contain excipients. Excipients include fillers, stabilizers, extenders, binders, humidifiers, surfactants, lubricants, and the like Excipients must be of sufficiently high purity and sufficiently low toxicity to render them suitable for administration to the animal being treated. An excipient can be inert or it can possess pharmaceutical benefits.

Excipients are selected with respect to the intended form of administration, e.g. oral tablets, capsules, powders, syrups, suspensions, and the like, and consistent with conventional pharmaceutical practices. For example, for oral administration in the form of gel capsule the omega-3 fatty acid formulation may be combined with a preservative, flavorant, colorant or the like.

The amounts of omega-3 formulation contained in an oral unit dose form for adult human patients may be generally varied or adjusted from about 400 mg to about 1000 mg of omega 3 fatty acids. For pediatric use an oral use the amount of omega 3 fatty acid contained in an oral unit dosage form will typically be less. Unit dosage forms for pediatric patients provide 10 mg/kg to about 30 mg/kg omega 3 fatty acid per day in one or two oral unit dosage forms. Thus, a unit dosage form for a child aged 2 to 6 years, contains about 50 mg to about 500 mg, or preferably about 150 to about 180 mg, omega-3 fatty acids. One or two unit dosage forms are provided daily to the pediatric patient. Particularly the invention includes oral dosage forms for use in adult humans in which the unit dosage form comprises at least 50 mg DHA and at least 300 mg EPA, at least 65 mg DHA and at least 330 mg EPA, at least 80 mg DHA and 350 mg EPA, at least 100 mg DHA and 400 mg EPA, or 125 mg DHA and 600 mg EPA. Dosage units prepared for human use may be used for veterinary purposes. However the invention also includes unit dosage forms prepared especially for veterinary use. Generally about 10 mg/kg to about 30 mg/kg should be administered daily for veterinary purposes. Thus unit dosage forms prepared for equine use having about 5 to about 15 g omega-3 fatty acids are included in the invention.

The invention provides a highly purified omega-3 fatty acid formulation comprising EPA and DHA in a weight to weight ratio from about 3.5:1 to about 6.99 to 1, from about 4.01:1 to about 6.99:1, or from about 4.01:1 to about 5:1. The invention also provides a highly purified omega 3 fatty acid formulation in which the weight to weight ratio of EPA:DHA is approximately 4.09:1. The EPA and DHA may be present in the formulation in either the triglyceride form or in the form of esterified fatty acid. Capsules typically contain the ethyl esters forms of EPA and DHA. Candy formulations typically contain the triglyceride forms of EPA and DHA.

The invention also provides highly purified omega-3 fatty acid formulations in which the content of EPA and DHA, taken together, is greater than 70%, greater than 75%, greater than 84%, or greater than 85% of the formulation by weight, and the omega-3 fatty acids comprise greater than 85%, greater than 90%, or greater than 91% of the formulation by weight. Additionally the invention provides omega-3 fatty acid formulations in which the amount of cholesterol in the formulation is less than 5% by weight, less than 2.5% by weight, or less than 1% by weight. The invention also includes omega-3 fatty acid formulations in which the formulation comprises less than 20 milliequivalents per kg peroxides, less than 10 milliequivalents per kg peroxides, or less than 5 milliequivalents per kg peroxides.

The invention includes solid dosages forms such as tablets and capsules. A capsule may be prepared, e.g., by placing the omega 3 fatty acid formulation, described above, inside a capsule shell. A capsule is a dosage form administered in a special container or enclosure containing an active agent. In some embodiments the omega-3 fatty acid is in liquid form and is filled into hard or soft capsules. A capsule shell may be made of methylcellulose, hydroxypropylmethyl cellulose, polyvinyl alcohols, or denatured gelatins or starch or other material. Hard shell capsules are typically made of blends of relatively high gel strength bone and pork skin gelatins. In some embodiments the unit dosage form is a gel capsule. In some embodiments the capsule shell is a glycerin capsule shell, for example product no. GSU0051 manufactured by SwissCaps and which meets USP 25 requirements (SwissCaps, USA 14193 SW 119th Ave., Miami/Fla., U.S. 33186). In other embodiments the capsule is a bovine gelatin shell, for example SwissCaps product no. GSU0708. Other suitable capsule shell materials include polyethylene, polypropylene, poly(methylmethacrylate), polyvinylchloride, polystyrene, polyurethanes, polytetrafluoroethylene, nylons, polyformaldehydes, polyesters, cellulose acetate, and nitrocellulose. The capsule shell itself may contain small amounts of dyes, opaquing agents, plasticizers, and preservatives. Conventional methods for preparing other solid dosage forms, for example, capsules, suppositories, and the like are also well known. Gelatin capsule shells may be made also be made of tapioca, grass, vegetable derived or fish derived gelatin. For example K-CAPS (Capsuline, Inc. Pompano Beach, Fla.) is a certified Kosher soft capsule shell of vegetable origin. Other vegetarian derived gelatin capsules may, be made of vegetable derived hyudroxypropylmethyl cellulose (HPMC). Capsules shells may also contain Modified Maize Starch, Glycerol, and Carrageenan as a gelling agent.

In other embodiments the capsule has a shell comprising the material of the rate-limiting membrane, including coating materials, and filled with Omega-3 fatty acids. Capsule shells may be made of a porous or a pH-sensitive polymer made by a thermal forming process. In certain embodiments the capsule shell in the form of an asymmetric membrane; i.e., a membrane that has a thin skin on one surface and most of whose thickness is constituted of a highly permeable porous material.

Yet another useful capsule, a "swelling plug device", can be used. Omega 3 fatty acids can be incorporated into a non-dissolving capsule-half of the device which is sealed at one end by a hydrogel plug. This hydrogel plug swells in an aqueous environment, and, after swelling for a predetermined time, exits the capsule thus opening a port through which the active agent can leave the capsule and be delivered to the aqueous environment. Preferred hydrogel-plugged capsules are those which exhibit substantially no release of active agent from the dosage form until the dosage form has exited the stomach and has resided in the small intestine for about 15 minutes or more, preferably about 30 minutes or more, thus assuring that minimal omega 3 fatty acid is released in the stomach. Hydrogel-plugged capsules of this type have been described in patent application WO90/19168, which is incorporated herein by reference.

Conventional methods for preparing tablets are known. Such methods include dry methods such as direct compression and compression of granulation produced by compaction, or wet methods or other special procedures.

Liquid form preparations include solutions, suspensions and emulsions. Examples of liquid pharmaceutical preparations include propylene glycol solutions and solutions containing sweeteners for oral solutions, suspensions and emulsions.

Omega-3 dosage forms may contain a plasticizer, particularly in a capsule shell. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose, and triacetin.

Omega-3 dosage forms described herein may be coated. The coating can be an enteric coating, i.e. a coating that is predominantly soluble in the intestinal fluid, but substantially insoluble in the gastric fluids. Examples of coating materials included polyvinyl acetate phthalate (PVAP), commercially available under trade names of Opadry® Enteric from Colorcon®, hydroxypropylmethylcellulose acetate succinate (HPMCAS), cellulose acetate phthalate (CAP), methacrylic acid copolymer, hydroxypropylmethylcellulose succinate, cellulose acetate succinate, cellulose acetate hexahydrophthalate, hydroxypropylmethylcellulose hexahydrophthalate, hydroxypropylmethylcellulose phthalate (HPMCP), cellulose propionate phthalate, cellulose acetate maleate, cellulose acetate trimellitate, cellulose acetate butyrate, cellulose acetate propionate, methacrylic acid/methacrylate polymer, methacrylic acid-methyl methacrylate copolymer, ethyl methacrylate-methylmethacrylate-chlorotrimethylammonium ethyl methacrylate copolymer, and the like, and combinations comprising one or more of the foregoing enteric polymers. Other examples include natural resins, such as shellac, SAN-DARAC, copal collophorium, and combinations comprising one or more of the foregoing polymers. Yet other examples of enteric polymers include synthetic resin bearing carboxyl groups. The methacrylic acid:acrylic acid ethyl ester copolymers are commercially available under the trade names of "Eudragit® L", such as Eudragit® L 30-D55 from Degussa.

Omega-3 formulations described herein may include a stabilizer. "Stabilizers" include compounds which maintain a desirable attribute of the formulation over a time interval including but not limited to mechanical, chemical and temperature stressing that can be tested in a laboratory setting. Such attributes include stabilizing homogeneity resulting in concentrations consistent with the labeled potency, maintaining specified purity and dispersibility in simulated gastric and intestinal fluids without significant degradation of the attributes for which the stabilizer was employed. In some embodiments the stabilizer is an antioxidant, such as vitamin E. Other suitable antioxidants include hydroxytoluene, butyrate, quinone, ascorbic acid.

Omega-3 formulations described herein may contain a preservative. Preservatives are compounds that inhibit microbial growth and are typically added to dispersions to prevent microbes from growing. Typically amounts of preservatives needed to pass anti-microbial effectiveness testing as described by USP and EU methodology are used to test appropriate preservative levels. Preservatives include but are not limited to potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Coloring agents provide coloration to the composition or dosage form. Such excipients can include food grade dyes and food grade dyes adsorbed onto a suitable adsorbent such as clay or aluminum oxide. The amount of the coloring agent can vary, for example from about 0.1 to about 5% by weight of the composition or from about 0.1 to about 1%.

Packaged Formulations

Packaged pharmaceutical formulations are included herein. Such packaged formulations include one or more omega-3 unit dosage forms in a container and instructions for using the dosage form to treat a patient having a disease or disorder responsive to omega-3 fatty acid treatment or in need of prophylactic omega-3 fatty acid therapy.

The invention includes providing prescribing information, over the counter medical use information, or nutritional information for the dosage form, for example, to a patient or health care provider, or as a label in a packaged pharmaceutical formulation. Information included in the pharmaceutical package may include for example efficacy, dosage and administration, contraindication and adverse reaction information pertaining to the omega-3 dosage form.

In certain embodiments the omega-3 dosage forms provided herein are omega-3 capsules provided in blister packages together with over the counter medical use information and/or nutritional information. Such packages may contain, for example 30, 60, or 180 omega-3 fatty acid unit dosage forms.

Packaged pharmaceutical formulations in which an omega-3 formulation described herein is the only active agent or in which an omega-3 formulation as described herein is packaged in combination with one or more other active agents are included in the invention.

Methods of Treatment

The invention includes methods of preventing and treating of cardiovascular disease, autoimmune disorders, inflammatory disorders, central nervous system disorders, and chronic pain by providing an omega-3 formulation as described herein to a patient in need thereof. The patient may be a human or non-human patient. Non-human patients include livestock animals, such as cattle, sheep, and horses and domestic companion animals, such as cats and dogs. In certain embodiments the non-human patient is a horse or dog.

Diseases and disorders that may be treated with the omega-3 fatty acid formulations described herein include alopecia, Alzheimer's dementia, anxiety disorders, asthma, attention deficit disorder, attention-deficit hyperactivity disorder, atopic dermatitis, autism, bipolar disorder, borderline personality disorder, cardiovascular disease, chronic fatigue syndrome, chronic pain, chronic polyarthritis, cognitive disorders, communication disorders, Crohn's disease, cystic fibrosis, dementia, depression, diabetes (of the non-insulin dependent or insulin dependent forms), diabetes-related sequelae, diabetic neuropathy, dry eyes and other inflammatory eye disorders, dry skin, dysmenorrhea, eating disorders (such as anorexia nervosa or bulimia nervosa and obesity), eczema, fibromyalgia, gout, learning disorders (e.g. reading, spelling, mathematics, receptive, and expressive language, and motor skills disorders), lupus, male infertility, metabolic syndrome, melanoma, mild cognitive impairment, migraine, mood disorders, multiple sclerosis, obsessive-compulsive disorder, oppositional-defiant disorder, osteoarthritis, osteoporosis, pervasive developmental disorders, polyarteritis nodosa, psoriasis, psoriatic arthritis, rheumatoid arthritis, schizophrenia, sclerodermia, self-injurious behavior, sickle cell anemia, tic disorders, ulcerative colitis, or vasculitic disorders (such as polyarteritis nodosa and temporal arthritis. Cardiovascular disease and disorders that can be treated with the omega-3 fatty acid formulations described herein include angina, atherosclerosis, hypercholesterolemia, hypertriglyceridemia, low HDL, high blood pressure, Raynaud's disease, and cardiac arrhythmias. Methods of treatment with the omega-3 fatty acid formulations described herein include prophylaxis with Omega-3 formulations to prevent post-cardiotomy (including but not limited to coronary artery bypass graft surgery and valve surgery) complications (including but not limited to depression, neuro-cognitive decline, congestive heart failure and infarction, clotting events, and arrhythmias) as well as for the treatment for such complications. The invention includes a method of preventing or reducing the risk a second myocardial infarction by providing an omega-3 formulation as described herein at least one time per day for at least 60 days, 180 days, 360 days, or in perpetuity to a patient following a first myocardial infarction.

The omega-3 fatty acid formulations described herein may be used to prevent basal cell carcinomas. In certain embodiments the omega-3 fatty acid formulations described herein are given to patients in remission from basal cell carcinoma, to reduce the risk of recurrence. The omega-3 fatty acid formulations described herein may be used to diminish weight loss cachexia associated with cancer treatment and to augment the effects of cancer chemotherapy.

The omega-3 formulations described herein may also be used in humans and animals for cosmetic purposes. For example the formulations may be used to improve skin quality and clarity and hair or coat shine.

Dosage levels of the order of from about 10 mg to about 35 mg per kilogram of body weight per day, about 14 mg to about 30 mg per kilogram of body weight per day, or 15 mg to about 25 mg per kilogram of body weight per day are useful in the treatment of the above-indicated conditions (about 500 mg to about 3 g per adult human patient per day or preferably about 1000 mg to about 200 mg per adult human patient per day). The amount of omega-3 fatty acid that may be combined with the carrier materials to produce a single unit dosage form will vary depending upon the host treated and the particular mode of administration. Dosage unit forms for adult human patients will generally contain between from about 500 mg to about 1500 mg of purified EPA and DHA. Dosage forms for pediatric or veterinary patients will contain different amounts of Omega-3 fatty acids. Frequency of dosage may also vary depending on the rout of administration and the particular disease treated. However, for treatment of most cardiovascular, central nervous system disorders, autoimmune system disorders and inflammatory disorders a dosage regimen of 4 times daily or less is preferred and a dosage regimen of 1 or 2 times daily or less is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

When the omega-3 formulations provided herein are used to treat central nervous system disorders, particularly psychiatric disorders, patients should be evaluated on a regular basis over an extended period of time, e.g. 1 to 12 weeks. One good method of carrying out evaluations is for patients to keep a daily diary in which they chart their moods. For example, patients may keep a daily record in which they rate their best and worst moods as either normal, mildly, moderately or severely depressed. These records should help the patient and their physician determine if depression occurs less frequently or becomes less extreme intensity. Ideally, such a diary should be kept both before and after the administration of omega-3 fatty acid is begun. The evaluation of mood alterations by the patient should also be supplemented with periodic clinical evaluations carried out by a physician. In some cases, the evaluation discussed above may indicate that mood fluctuations have become so stabilized in a patient as the result of administering omega-3 fatty acid at the initial concentration that no further adjustment in dosage is necessary. In other cases, the dosage of omega-3 fatty acid may be increased in order to obtain a more efficacious result. In general, dosage should not be increased beyond the point at which further stabilization of patient mood is observed. If patients experience adverse side effects, then dosages may be adjusted in a downward direction accordingly.

When treating depression in a human patient, an effective amount of an omega-3 fatty acid formulation as described herein, in certain embodiments, is an amount sufficient to decrease the patient's HAM-D scores. The HAM-D (Hamilton Depression) rate scale is a numerical scoring of depression symptoms that provides an indication of depression and over time provides a guide to treatment progress. A HAM-D score of 10-13 indicates mild depression, 14-17 indicates mild to moderate depression and a score of greater than 17 indicates severe depression.

When treating a cardiovascular disorder an effective amount of an omega-3 fatty acid formulation as described herein is, for example, an amount sufficient to decrease diastolic or systolic blood pressure, decrease pulse rate, decrease serum cholesterol, reduce serum triglycerides, or reduce the activity of coagulation factor VII is considered and effective amount of the formulation.

The process of adjusting dosage in an upward or downward direction and evaluating the effect of the adjustment on mood changes should be continued until an optimum dosage is discovered, i.e. the dosage at which the patient experiences the best balance between therapeutic effectiveness and discomfort due to side effects. In cases where adverse side effects are not experienced, the optimal dosage is the lowest dose resulting in maximum reduction in psychiatric episodes.

Combination Administration

The Omega-3 fatty acid formulations and dosage forms provided herein may be used alone or in combination with one or more other active agents. For example the omega-3 fatty acid formulations provided herein may be used with other psychotropic agents including, for example, lithium, pharmaceutical antidepressants, herbal antidepressants (e.g., St. John's Wort, S-adenosylmethionine), anti-convulsants, mood stabilizers, antipsychotic agents, benzodiazepines, psychostimulants, and alpha-2 agonists. These other agents may either be given together with omega-3 fatty acid in a single dosage form, or they may be administered separately.

The omega-3 formulations described herein may also be provided in combination with active agent used to treat cardiovascular disorders. Particularly the omega-3 formulations may be used in combination with agents used to treat dyslipidemia, for example the formulations may be used in combination with statins, fibrates, and bile acid binding resins, including atorvastatin calcium (LIPITOR), fenofibrate (TRICOR), simvastatin (ZOCOR), pravastatin (PRAVACHOL), ezetimibe (ZETIA), ezetimibe/simvastatin (VYTORIN), and clopidpgrel bisulfate (PLAVIX). The omega 3 formulations described herein may also be used in combination with other classes of agents used to treat cardiovascular disorders including diuretics, calcium channel blocker, antianginal drugs, cardiac iontropic agents such as digoxin, antihypertensive, antiarrhythmics such as Amiodarone, beta blockers, and ACE inhibitors.

In certain embodiments, patients taking anti-depressants will continue taking other active agents they have been taking prior to omega-3 fatty acid treatment during the time at which omega-3 fatty acid treatment is begun. Optimal dosages for each of the drugs may then be determined sequentially. For example, administration of one agent may be initiated and then optimized followed by the initiation and optimization of omega-3 fatty acid treatment. The problem of adjusting the dosages of multiple therapeutic agents is one that is routinely encountered by physicians and can be solved using well-established procedures similar to those discussed herein.

The omega-3 fatty acid formulations described herein may also be provided in combination with vitamins or herbal supplements either in a single unit dosage form or in separate unit dosage forms. For example the omega-3 fatty acid formulations may be provided in combination with ascorbic acid, folic acid, Vitamin A, Vitamin C, Vitamin D, Vitamin E, Vitamin B12, Vitamin K, Thiamin, Riboflavin, Niacin, Vitamin B6, Biotin, or pantothenic acid.

EXAMPLES

Example 1

Fish Oil Refinement to Provide Highly Purified Omega 3 Fatty Acids

Manufacture Under Nitrogen

The manufacturing process is carried out under nitrogen conditions, with packing under vacuum, to limit any oxidation of the fish oil by its exposure to air. This process preserves the freshness of the Omega-3 product and eliminates the emergence of any oxidative contaminants.

This process includes refinement of crude fish oil. Crude fish oil is obtained by methods known to those of ordinary skill in the art.

Degumming, Deacidifcation and Bleaching

The crude fish oil undergoes a pre-treatment prior to other steps in the refining process. This might be considered a 'general pre-treatment' of the crude fish oil. In this process, phospholipids, metals, pigments, carbohydrates, proteins, fatty acids, sulfur, oil-insolubles, and oxidation products are removed.

Adsorbent Treatment

Adsorbent treatment is carried out by methods know to those of ordinary skill in the pharmaceutical arts. In this process heavy metals (such as mercury, cadmium, arsenic, copper and lead), PCBs, organo-chlorins, and dioxins (PCDD/PCDF) are removed.

Ethyl-Esterification

In this process, the triglyceride (TG) form of fish oil is converted into the ethyl-ester form of fish oil to concentrate the EPA and/or DHA in the fish oil. Methods for converting triglyceride form of fish oil to the ethyl ester form.

For example, crude fish oil may be diluted with ethanol, and then refluxed in the presence of catalytic amounts of concentrated sulfuric acid. After extraction with hexane, the transesterification mixture is subjected to silica gel chromatography, then to a two-step molecular distillation process, with a vacuum of about 10-3 mm Hg and at an evaporation temperature ranging from 65.degree.-70.degree. C. to 105.degree.-125.degree. C. and a condenser at 5.degree. C.

This process optimizes Omega-3 purity and provides maximal concentrations of EPA and DHA, the Omega-3 essential fatty acids with demonstrated clinical benefits.

Recrystallization

Recrystallization is used to increase the concentration of omega-3 fatty acids in the fish oil by removing saturated fatty acids.

Molecular Distillation

Molecular distillation is effected by heating the recrystallized fish oil to a temperature sufficient to evaporate unnecessary fatty acids. The process environment is less than a 0.1 torr vacuum. This process step increases the concentration of EPA and/or DHA and removes potential environmental contaminants such as heavy metals.

High Vacuum Distillation

This step is a type of fractionation process, in which ethyl esters in the fatty acids are separated and purified. This unique process allows for provides purified omega 3 fatty acids having and EPA to DHA ration of over 4:1. This specialized process is performed under a 0.1 torr vacuum condition, and allows for further elimination of PCBs, organo-chlorins, and dioxins (PCDD/PCDF).

The multiple sequential steps of purification allow for a maximally concentrated Omega-3 product, with greater than 91% Omega-3 fatty acids and an approximately 85% EPA+DHA concentration (higher concentration on independent testing). Moreover, the processes that enhance Omega-3 purity and concentration also eliminate environmental contaminants that may have been present in the crude fish oil.

Example 2

Enhanced Mood, Cognitive Functioning, Energy Level and Decreased Anxiety Associated with OMAX3 (91% Pure Omega-3-Acid Ethyl Ester; 4.09:1 Ratio of EPA:DHA) Treatment but not with Previous Treatment Using an Approximately 30% Pure Omega-3 Fatty Acid and 1.4:1 Ratio of EPA:DHA Supplement Ms. A was a 23 year old Caucasian woman with a history of major depressive disorder (MDD), generalized anxiety disorder (GAD), obsessive-compulsive disorder (OCD) and borderline personality disorder who was refractory to standard medication regimens. She previously failed multiple trials of antidepressant medications and augmentation strategies. Her depressive and anxiety symptoms impaired her ability to function, and she had to drop out of college due to her symptoms. She also engaged in self-injurious behaviors (cutting self) and spent excessive time engaged in obsessive-compulsive behaviors.

Ms. A was previously treated with multiple medication trials and previous attempts at behavior modification. Ms. A's current medications included Adderall XR 30 mg a day, Adderall 10 mg each afternoon as needed, Lamictal to 200 mg a day, lithium 300 mg two tablets at bedtime and one in the morning, Prozac 80 mg a day, and trazodone 50 mg q.h.s. Additionally, she had two prior failed trials of treatment with over-the-counter fish oil supplements. The omega-3 purity of the prior fish oil supplements was approximately 30% omega-3 fatty acids per capsule, 2 gram total dose, and a 1.4 ratio of EPA:DHA. Ms. A showed no significant change in her symptoms after being treated with the two prior fish oil supplements.

Ms. A presented to our clinic seeking help for these severe and treatment refractory mood and anxiety disorder symptoms. Diagnosis of MDD and OCD was confirmed using the Structured Clinical Interview for DSM-IV Axis I Disorders-Clinician Version. After informed consent, Ms. A was treated clinically by adding the health supplement, OMAX3 (91% pure omega-3-acid ethyl ester; approximately 4.09:1 ratio of EPA:DHA; 1650 mg per day fish oil, with, respectively, 1500 mg Omega-3 essential fatty acids, 1125 mg EPA, and 275 mg DHA), to her medication regimen. Within 3 weeks of treatment with OMAX3, Ms. A demonstrated a significant clinical improvement in her mood and anxiety symptoms. More specifically, she reported a remission of depressive symptoms, significantly decreased anxiety, feelings of improved cognitive clarity, enhanced mood, increased energy level, decreased fatigue, enhanced cognition/attention and decreased OCD symptoms. She also reported a cessation of self-injurious behavior. Her clinical improvement in symptoms was also objectively observed by an approximately 79% reduction in her HAM-D scores (pre-OMAX3 treatment versus post-4 weeks of OMAX3 treatment). These results are presented in FIG. 1. Ms. A experienced a dramatic improvement in her level of functioning and was able function at her job and also return to college studies. She remarked that the change in her symptoms when treated with OMAX3 was remarkable compared to the lack of treatment response to her prior treatment with the less pure and 1.4:1 ratio of EPA:DHA fish oil supplement that she had been treated with in the past.

Example 3

Gelatin Capsule Containing Highly Purified Omega-3 Fatty Acids

The formulation for an 825 mg capsule containing highly purified omega-3 fatty acids is given in Table I. This product is manufactured according to the procedure set forth in Example 1.

TABLE I

| Component | Amount per 825 mg capsule | Amount in total daily dose (2 capsules) | Weight percent of capsule, excluding capsule shell |
|---|---|---|---|
| EPA ethyl ester | 562.5 mg | 1125 mg | 68.2% |
| DHA ethyl ester | 137.5 mg | 275 mg | 16.7% |

TABLE I-continued

| Component | Amount per 825 mg capsule | Amount in total daily dose (2 capsules) | Weight percent of capsule, excluding capsule shell |
|---|---|---|---|
| Other omega-3 fatty acids | 50 mg | 100 mg | 6.1% |
| Vitamin E (as d-alpha-tocopherol) | 5 IUs | 10 IUs | |

Omega-3 fatty acid ethyl esters are derived from deep sea fish oil, purified by the method outlined in Example 1. The EPA:DHA ratio is 4.09:1 with a range of 4.05-4.20:1. Two capsules daily provides a single daily dose of omega-3 fatty acids. Vitamin E is added as a stabilizer and antioxidant to preserve product freshness. The formulation contains no, or negligible, cholesterol and no or negligible saturated fat. Peroxide levels are a measure of freshness. The formulation contains less than 5 milliequivalent per kg peroxide. Anisidine value (AV) is less than 20. TOTOX value is less than 26 [calculated as (2×PV)+AV].

The formulation contains less than 0.025 ppm mercury. No other heavy metals (i.e. cadmium, arsenic, or lead) are detectable. The formulation contains less than 0.09 mg/kg (ppm) total PCBs. Total PCBs are calculated at the sum of four non-ortho PCBs and eight mono-ortho PCBs. When tested for dioxins (the sum of 17 individual dioxin congeners) the formulation is found to contain not more than 2 TEF/g (toxic equivalent factors as defined by the World Health Organization). The product meets GMP standards. The product is manufactured and encapsulated under nitrogen to prevent oxidation.

Example 4

Treatment of Alopecia in Male Caucasian Patient with 91% Pure Omega-3-Acid Ethyl Ester; 4.09:1 Ratio of EPA:DHA An omega-3 fatty Acid formulation of 91% pure Omega-3 acid ethyl ester, 85% EPA and DHA, with an EPA:DHA ratio of 4.09:1 was administered orally (daily dose 1500 mg omega-3 fatty acids) to male Caucasian patient exhibiting male pattern baldness for 87 days. FIG. 2 shows hair growth before omega-3 fatty acid treatment, after 41 days of treatment and after 87 days treatment. The patient experienced significant hair growth after 41 days treatment and continued improvement of hair growth after 87 days of treatment.

Example 5

Improvement in Cognition, Attention, and Tics After Treatment with OMAX3

Mr. R is a 22 year old male with a history of major depression (recurrent), Attention Deficit Hyperactivity Disorder (ADHD)—combined type, and Tic Disorder, Not Otherwise Specified. Mr. R had multiple medication trials for his ADHD beginning at the age of 13. Past medication trials included: Strattera (atomoextine), Adderall, Adderall XR, methylphenidate, Tenex (guanfacine), and Concerta. His most recent medication treatment was with Concerta 54 mg per day. Medication treatment for his major depression included Zoloft and Celexa, though the patients' depressive symptoms stabilized by his junior year of college and he was taken off all antidepressant medications.

Mr. R's Tic Disorder was comprised of both vocal and motor tics in the form of random verbalizations or screeching sounds, as well as either a facial and neck twitch. His tics would occur at least several times per week, typically not in relation to one another, could be consciously suppressed and, by his account, were present probably since before middle school. The use of Risperdal (risperidone) and Tenex (guanfacine) were utilized to help address his tics in the past, with only a partial treatment response and poor tolerability. A baseline clinical evaluation, based on patient's self-report of symptoms, indicated that the patients tic symptoms were of moderate severity, occurring 4-5 days per week, several times per day, for a significant period of time. His inattention symptoms were mild-moderate, by his report, sufficiently improved with Concerta from his pre-existing baseline, so that the patient was able to manage a fairly heavy college academic workload with some intermittent difficulty. Hyperactivity symptoms were, also by his report, at a mild/moderate level compared to a pre-existing baseline.

The patient was treated with OMAX3, 2 capsules per day (1125 mg EPA, 275 mg DHA, 1500 mg Total Omega-3 fatty acids) for the purpose of enhancing his attention and cognitive function. Six weeks into augmentation with OMAX3, the patient experienced an enhanced ability to focus and concentrate. There was clinically significant improvement in the following areas: less distractibility, better written and expressive language function, diminished forgetfulness, and improvement in his sense of restlessness. The frequency of his tics, of both the motor and vocal form, were markedly diminished and infrequent. The patient's improvement in cognition, attention and attenuation of tics was accompanied by no adverse effects from the OMAX3.

Example 6

Decreased Obsessive Compulsive Disorder Symptoms Following Treatment with 91% Pure Omega-3-Acid Ethyl Ester; 4.09:1 Ratio of EPA:DHA (OMAX3)

Mr. W is a 30 year old white male with a long history of chronic obsession (about sexual urges, death, and illness) as well as compulsions, including hand washing and repetitive motions. Mr. W. was recalcitrant to treatment with antianxiety medications including benzodiazepines, antidepressants (including SSRIs and SNRIs), and the anti-psychotic, olanzapine. He was a administered a high daily dose of OMAX3 (greater than 3 g/day). Patient W. demonstrated a remissions of 2 of the 3 obsessions and significant improvement in his compulsive activity. Symptom decrease began after 1 week of treatment and has been maintained as of 5 months of OMAX3 administration.

Example 7

Increased HDL and Decreased Triglyceride Levels After 8 Weeks of Treatment with OMAX3 (91% Pure Omega-3-Acid Ethyl Ester; 4.09:1 Ratio of EPA:DHA)

Ms. B was a 53 year old Caucasian woman with a history of cardiovascular disease who presented to clinic with borderline high blood sugar (her fasting blood sugar was 150 mg/dL [normal range=70-99 mg/dL] and dyslipidemia (her HDL was 30 mg/dL [normal range>=39]; triglycerides were 360 mg/dL [normal range=30-180]). She was started on OMAX3 (91% omega-3 acid ethyl ester) at a daily dose of 3300 mg.

After 8 weeks of treatment with OMAX3, she returned to clinic for follow-up and laboratory analysis revealed significantly lowered triglycerides and increased HDL. Her HDL increased to 48 mg/dL [normal range>=39] and triglycerides decreased to 180 mg/dL [normal range=30-180]. Additionally, her blood sugar level decreased to 108 mg/dL.

What is claimed is:

1. A pharmaceutical or drug formulation comprising eicosapentanoic acid (EPA) and docosahexanoic acid (DHA) in a weight to weight ratio of about 3.5:1 to about 5:1, and wherein the formulation is more than 84% combined EPA and DHA by weight and wherein said formulation comprises no active ingredients other than omega-3 fatty acids in the formulation.

2. The formulation of claim 1, wherein the EPA and DHA are in the ethyl ester form.

3. The formulation of claim 1 comprising EPA and DHA in a weight to weight ratio of about 4:1 to about 5:1.

4. The formulation of claim 1, wherein the weight to weight ratio of EPA to DHA is approximately 4.1:1.

5. The formulation of claim 1 wherein EPA and DHA are present in a weight to weight ratio of 4.8:1.

6. The formulation of claim 1, wherein said formulation is provided in a unit dosage form comprising at least 100 mg DHA and at least 400 mg EPA.

7. The formulation of claim 1, wherein said formulation is provided in a unit dosage form comprising at least 125 mg DHA and 600 mg EPA.

8. The formulation of claim 1, wherein the formulation additionally comprises a stabilizer.

9. The formulation of claim 5, wherein the stabilizer is vitamin E.

10. The formulation of claim 1, wherein the formulation is more than 90% omega-3 fatty acids by weight.

11. The formulation of claim 1, wherein the formulation comprises less than 1% cholesterol.

12. The formulation of claim 1, wherein the formulation comprises less than 10 meq/kg peroxides.

13. A pharmaceutical or drug product, comprising the formulation of claim 1 in a package together with instructions for using the formulation to treat a cardiovascular disorder, depression, or inflammatory disorder.

14. The pharmaceutical or drug product of claim 13, wherein the formulation is in a dosage form of a gel or liquid capsule packaged in a blister package.

15. A method of treating cardiovascular disease, depression, or inflammatory disorders by providing an effective amount of the formulation of claim 1 to a patient in need thereof.

16. The method of treating of claim 15, wherein the cardiovascular disease is dyslipidemia.

17. A method of treating a cardiovascular surgical complication by providing an effective amount of the formulation of claim 1 to a patient in need thereof prior to, or after, a cardiovascular surgical procedure being performed on the patient, and wherein the complication is depression.

18. The method of claim 17, wherein the surgical procedure is cardiotomy and the complication is post-cardiotomy depression.

19. The method of reducing the risk of a second myocardial infarction in a patient by providing to the patient the pharmaceutical formulation of claim 1 at least one time per day for at least 60 days following the experience of first myocardial infarction.

20. The method of treating of claim 19, wherein 750 to 3000 mg of the formulation is provided to said patient daily.

21. The formulation of claim 1, wherein the formulation is consisting essentially of omega-3 fatty acids.

22. A method of simultaneously treating cardiovascular disease, depression, and inflammatory disorders by providing an effective amount of the formulation of claim 1 to a patient in need thereof.

23. A method of simultaneously treating cardiovascular disease, depression, and inflammatory disorders by providing an effective amount of the formulation of claim 3 to a patient in need thereof.

24. The method of simultaneously treating cardiovascular disease, depression, and inflammatory disorders according to claim 23, wherein said cardiovascular disease is dyslipidemia.

25. The method of treating of claim 16, wherein said dyslipidemia includes one or more of hypertriglyceridemia or low HDL.

26. A method of treating dyslipidemia by providing an effective amount of the formulation of claim 1 to a patient in need thereof.

27. The method of treating of claim 26, wherein said dyslipidemia includes one or more of hypertriglyceridemia or low HDL.

* * * * *